United States Patent [19]

Bizen et al.

[11] Patent Number: 5,073,316

[45] Date of Patent: Dec. 17, 1991

[54] PROCESS FOR PRODUCING A POROUS FILM

[75] Inventors: Kunio Bizen, Kurashiki; Minoru Kashino, Yokohama; Tasuku Suzuki, Kurashiki; Ryuichi Hasegawa; Koji Hayashi, both of Kuwana, all of Japan

[73] Assignees: Mitsubishi Kasei Vinyl Company; Mitsubishi Kasei Corporation, both of Tokyo, Japan

[21] Appl. No.: 593,563

[22] Filed: Oct. 9, 1990

Related U.S. Application Data

[63] Continuation of Ser. No. 236,751, Aug. 26, 1988, abandoned.

[30] Foreign Application Priority Data

| Aug. 27, 1987 | [JP] | Japan | 62-213747 |
| Oct. 8, 1987 | [JP] | Japan | 62-253958 |
| Mar. 17, 1988 | [JP] | Japan | 63-64405 |

[51] Int. Cl.$^5$ ............................................. B29C 67/20
[52] U.S. Cl. .................................... 264/22; 264/26; 264/41; 264/80; 264/210.6; 264/210.7; 264/288.8; 264/290.2
[58] Field of Search ............... 264/41, 288.8, 290.2, 264/22, 26, 80, 210.6, 210.7; 106/122

[56] References Cited

U.S. PATENT DOCUMENTS

| 4,076,656 | 2/1978 | White et al. | 106/122 |
| 4,472,328 | 9/1984 | Sugimoto et al. | 264/41 |
| 4,767,580 | 8/1988 | Shingo et al. | 264/41 |
| 4,794,128 | 12/1988 | Vawaguchi et al. | 521/138 |

FOREIGN PATENT DOCUMENTS

| 66672 | 12/1982 | European Pat. Off. . |
| 57-47334 | 3/1982 | Japan . |
| 57-203520 | 12/1982 | Japan . |
| 58-15538 | 1/1983 | Japan . |
| 58-149925 | 9/1983 | Japan . |
| 59-62117 | 4/1984 | Japan . |
| 59-136334 | 8/1984 | Japan . |
| 59-140235 | 8/1984 | Japan . |
| 60-229731 | 11/1985 | Japan . |
| 60-230825 | 11/1985 | Japan . |
| 61-144331 | 7/1986 | Japan . |
| 61-235439 | 10/1986 | Japan . |
| 62-10141 | 1/1987 | Japan . |
| 62-18435 | 1/1987 | Japan . |
| 62-27438 | 2/1987 | Japan . |
| 62-101415 | 5/1987 | Japan . |
| 62-129321 | 6/1987 | Japan . |
| 62-280235 | 12/1987 | Japan . |
| 62-2280234 | 12/1987 | Japan . |
| 62-6288640 | 12/1987 | Japan . |
| 63-22844 | 1/1988 | Japan . |
| 63-251436 | 10/1988 | Japan . |

Primary Examiner—Hubert C. Lorin
Attorney, Agent, or Firm—Oblon, Spivak, McClelland, Maier & Neustadt

[57] ABSTRACT

A process for producing a porous film comprising polyolefin resin, a filler and an ester of dipentaerythritol having a ratio 3 to 70% residual OH groups.

17 Claims, No Drawings

PROCESS FOR PRODUCING A POROUS FILM

This application is a Continuation of application Ser. No. 07/236,751, filed on Aug. 26, 1988, now abandoned.

BACKGROUND OF THE INVENTION

The present invention relates to a porous film, a process for producing the same and absorbent sanitary articles. Particularly, the present invention relates to a porous film composed of polyolefin resin, a filler and an ester of dipentaerythritol having 0 to 70% residual OH groups, which has a good appearance and feeling, excellent strength and proper moisture permeability, a process for producing the porous film with a high efficiency, and absorbent sanitary articles such as a disposable diaper or a sanitary absorbent (napkin) using the porous film. Further, the porous film can be applied to various uses such as clothing, packaging media, battery separators, filtering media and sanitary and medical materials.

Many attempts to uniaxially or biaxially stretch the film obtained by mixing polyolefin resin with a filler and then melt-molding the obtained mixture have been previously made as means for producing porous films. However, in these porous films, the uniaxially stretched film still has problems with respect to the anisotropy in the physical properties thereof, particularly the tear strength in the longitudinal direction (stretching direction), and the surface strength. The biaxially stretched film has no problem with respect to the anisotropy in the physical properties thereof, but does have problems with respect to the stretching property and the surface strength. In addition, both films generally show a high stiffness which is a disadvantage according their uses.

A method of improving the anisotropy in the physical properties of a film and the surface strength thereof is stretching with as low a ratio as possible to form a porous film. A method in which a low-melting point polymer, a rubber substance, a plasticizer or a surfactant is added can be considered as a method of giving flexibility to the film. However, no porous film which satisfies the balance of physical properties of molding stability, porosity, stretching property, mechanical properties such as tear strength and tensile strength, and surface strength has been found.

As a method for improving the aforementioned disadvantages of conventional porous films, a composition obtained by mixing polyolefin resin, a filler and liquid polybutadiene or liquid polybutene (Japanese Patent Application Laid-Open (KOKAI) No. 57-47334) and a composition obtained by mixing linear low-density polyethylene, a filler and a polyhydroxy saturated hydrocarbon (Japanese Patent Application Laid-Open (KOKAI) No. 58-15538) have been proposed.

In addition, a method of using a polyester plasticizer such as an adipate or an epoxy plasticizer such as epoxidized soybean oil has also been proposed in Japanese Patent Application Laid-Open (KOKAI) No. 61-144331(1986), methods of using triglyceride have been proposed in Japanese Patent Application Laid-Open (KOKAI) Nos. 62-10141(1987) and 62-18435(1987), and a method of using silicone oil has been proposed in Japanese Patent Application Laid-Open (KOKAI) No. 62-129321(1987).

Methods of using ester compounds have also been proposed in Japanese Patent Application Laid-Open (KOKAI) Nos. 61-235439(1986), 62-18435(1987), 62-27438(1987), 62-280234(1987), 62-280235(1987), 62-288640(1987) and 63-22844(1988).

However, none of these methods has achieved a porous film which satisfies all the properties of a film such as the strength, permeability, flexibility, appearance, feeling, printing properties, etc.

Besides, a disposal diaper and an absorbent (hereinafter referred to as "diaper and the like") comprise a liquid permeable surface sheet such as a gauze or a non-woven fabric which directly contacts with a skin and a liquid absorbent such as a pulp paper or an absorbent polymer sheet, and a liquid impermeable back sheet used for preventing any leakage of a liquid. Recently, such diaper and the like have become remarkably popular owing to their convenience.

Although a polyethylene film is generally used as the liquid impermeable back sheet, the polyethylene film has no permeability to air and water vapor, and easily becomes stuffy. In order to solve this problem, it has been proposed to use a porous film permeable to water vapor and impermeable to a liquid (Japanese Patent Application Laid-Open (KOKAI) Nos. 58-149303(1983), 60-185803(1985) and 59-69906(1984)). In each of these Japanese Patent Applications Laid-Open (KOKAI), a porous film obtained by kneading polyolefin resin, an inorganic filler and a plasticizer, forming a film from the obtained mixture and stretching the film formed is used. A diaper and the like using such a porous film have an advantage in that the stuffiness is improved.

However, such a porous film has disadvantages in that, according to the kind of the plasticizer used, sufficiently uniform pores are not obtained and stretching spots are produced because of its poor stretching property, the porous film has poor flexibility, feeling and touch, and lacks in tear strength and tensile strength, and an eruption of the skin can occur due to bleeding of a plasticizer on the film surfaces with the passage of time. Therefore, a diaper and the like which can solve all of various problems with respect to the film strength, permeability, appearance and feeling have not been attained.

Further, the following inventions have been proposed: Japanese Patent Applications Laid-Open (KOKAI) Nos. 57-203520(1982), 58-149925(1983), 59-62117(1984), 59-136334(1984), 59-140235(1984), 60-229731(1985), and 60-230825(1985), and Japanese Patent Application No. 62-85219.

As a result of the inventors' studies with a view to solving the above-described problems, it has been found that a porous film obtained by melt-molding a composition composed of polyolefin resin, a filler and an ester of dipentaerythritol having 0 to 70% residual OH groups, and stretching the molded product, resulting in a good balance between the mechanical properties such as tear strength and tensile strength, and permeability to water vapor, and good flexibility, and that a diaper using the above-mentioned porous film as a liquid impermeable back sheet exhibits excellent strength, permeability, appearance and feeling. The present invention has been achieved on the basis of these findings.

It is an object of the present invention to provide a porous sheet which exhibits good extruding properties in melt-molding, particularly excellent stability in molding and which produces a uniaxially stretched product having a good balance between mechanical properties such as tear strength and tensile strength, and permeability to water vapor, uniaxially and biaxially stretched products both having high surface strength and good stretching properties, particularly few stretching spots which occur owing to non-uniform stretching during stretching with a low ratio as well as exhibiting good flexibility.

It is another object of the present invention to provide a disposable diaper and the like which can solve various problems with respect to film strength, permeability, appearance and feeling.

SUMMARY OF THE INVENTION

In a first aspect of the present invention, there is provided a porous film comprising of polyolefin resin, a filler and an ester of dipentaerythritol having 0 to 70% residual OH groups.

In a second aspect of the present invention, there is provided a process for producing a porous film comprising melt-molding a composition containing polyolefin resin, a filler and an ester of dipentaerythritol having 0 to 70% residual OH groups; and stretching the obtained sheet.

In a third aspect of the present invention, there is provided an absorbent sanitary articles comprising a liquid permeable surface sheet, a liquid absorber and a liquid impermeable back sheet of a porous film comprising polyolfin resin, a filler and an ester of dipentaerythritol having 0 to 70% residual OH groups, said liquid absorber being interposed between said liquid permeable surface sheet and said liquid impermeable back sheet.

DETAILED DESCRIPTION OF THE INVENTION

As a polyolefin resin used in the present invention high-density polyethylene, medium-density polyethylene and linear low-density polyethylene are used singly or in a mixture of two or more polymers. The melt index of such polyethylene is preferably within the range of 0.01 to 10 g/10 minutes, preferably 0.03 to 5.0 g/10 minutes (measured with 2.16 Kg at 190° C. in accordance with ASTM D-1238-70). Such polyethylene may contain branched low-density polyethylene which is obtained by a high-pressure method.

Crystalline polypropylene can also be used as the polyolefin resin of the present invention. As the crystalline polypropylene, propylene homopolymers or copolymers of propylene with other α-olefins are used singly or in a mixture of two or more polymers. It is possible to mix such polyolefin resins with additives such as heat stabilizers, ultraviolet absorbers, antistatic agents, pigments and fluorescent agents.

As a filler, an inorganic filler or an organic filler is used. As inorganic fillers that may be used in the present invention, calcium carbonate, talc, clay, kaolin, silica, diatomaceous earth, magnesium carbonate, calcium sulfate, aluminium hydroxide, zinc oxide, magnesium hydroxide, calcium oxide, magnesium oxide, titanium oxide, alumina, mica, asbestos powder, glass powder, shirasu ballon, zeolite and silicate clay may be exemplified. Calcium carbonate, talc, clay, silica, diatomaceous earth and barium sulfate are preferable.

As organic fillers that may be used in the present invention, cellulose powder such as wood powder and pulp may be exemplified. These fillers may be used singly or in a mixture.

The average particle size of a filler is preferably not more than 30 μm, more preferably not more than 10 μm, most preferably not more than 5 μm. If the particle size is too large, the denseness of the pores in a stretched film deteriorates. The surface treatment of a filler is preferable from the view point of dispersion in resin and stretching properties of the film. The surface treatment with a fatty acid or a metal salt thereof is preferred. The amount of the fatty acid or the metal salt thereof used in surface treatment is preferably not more than 10 parts by weight based on 100 parts by weight of the filler. The surface treatment with a large amount of such an agent is undesirable because white smoke generates or foaming takes place during kneading, pelletization or molding.

An ester of dipentaerythritol used as a third component in the present invention is an ester of dipentaerythritol and a carboxylic acid or a partial ester of dipentaerythritol and a carboxylic acid. Typical examples of carboxylic acids include aliphatic mono- or dicarboxylic acids having 1 to 30 carbon atoms and aromatic mono- or dicarboxylic acids having 7 to 16 carbon atoms. Aliphatic monocarboxylic acids are particularly preferable from the viewpoint of theri molding properties and stretching properties.

As carboxylic acids, aliphatic carboxylic acids such as acetic acid, propionic acid, butyric acid, isobutyric acid, valeric acid, isovaleric acid, capronic acid, isocapronic acid, 2-ethylbutanoic acid, enanthic acid, caprilic acid, lauric acid, tridecanoic acid, myristic acid, pentadecanoic acid, palmitic acid, stearic acid, eicosanoic acid, behenic acid, cerotic acid, melissic acid, succinic acid, glutaric acid, adipic acid, azelaic acid and sebacic acid; and aromatic carboxylic acids such as benzoic acid, phthalic acid, isophthalic acid and terephthalic acid may be exemplified. In the case of a monomolecular partial ester of dipentaerythritol, the above-described monocarboxylic acids can be used singly or in a mixture. When a dicarboxylic acid is used, the amount of the carboxylic acid used is preferably at most 0.5 mole per mole of dipentaerythritol, and the remaining hydroxyl groups are reacted with a monocarboxylic acid in an amount of the corresponding moles to form a partial ester.

The ratio of the residual OH groups in the esterified product of dipentaerythritol is within the range of 0 to 70%, preferably 3 to 70%, more preferably 3 to 50% of the OH groups in one molecule thereof. If the ratio is 3% or more, the effect of improving stretching properties and printing properties is more excellent, while if the ratio is over 70%, the film forming properties of a film deteriorate.

Methods of producing the ester of dipentaerythritol of the present invention, a method in which dipentaerythritol is reacted with a slightly excessive amount of carboxylic acid, the reaction is stopped when the degree of esterification increases to a target value, and the excessive carboxylic acid is extracted to obtain a product; and a method in which amounts of raw materials necessary for a theoretical structre are introduced, and dehydration reaction is completed to form a product. In the latter method, it is preferable to use an entrainer in order to increase the effect of dehydration.

With respect to the compounding ratios of the polyolefin resin, the filler and the ester of dipentaerythritol as a third component, the amount of the filler used is preferably within the range of 25 to 400 parts by weight, more preferably within the range of 100 to 300 parts by weight based on 100 parts by weight of the polyolefin resin, and the amount of the used ester of dipentaerythritol is preferably within the range of 1 to 30 parts by weight, more preferably within the range of 3 to 20 parts by weight based on 100 parts by weight of the polyolefin resin.

If the amount of the filler compounded is too small, pores are not sufficiently formed in a stretched film, resulting in a decrease in the porosity of the film. While if the amount of the filler compounded is to large, the kneading properties and dispersion are impared, resulting in deterioration of the moldability of a film and decrease in the surface strength thereof. If the amount of the third component compounded is too large, satisfactory kneading properties cannot be obtained, and as a result sufficient moldability and stretchability cannot be secured.

The mixing of the polyolefin resin, the filler and the third component is performed by using a ordinary blender or a mixer.

A drum- or tumbler-type mixer, a ribbon blender, a Henschel mixer or a super mixer is used as the mixer, but a high-speed stirring machine such as Henschel mixer is preferable.

The kneading of the obtained mixture is appropriately performed by using a known apparatus such as an ordinary screw extruder, a biaxial screw extruder, a mixing roll, a Banbury mixer or a biaxial kneader.

The forming of a film may be performed by using an ordinary film-forming apparatus in accordance with an ordinary method for forming a film. Blown film extruding using a circular die or T-die extrusion molding may be suitably employed in the forming of a film.

The thus-formed film is then stretched at a temperature of 40° to 170° C., preferably 40° to 80° C. In the case of uniaxial stretching, roll stretching is generally used. Also, a method in which stretching in the uniaxial direction (machine direction) is relatively strengthened by tubular stretching may be used and stretching may be performed in one stage or multiple stages of two or more stages.

In biaxial stretching, low-ratio stretching can be performed in either simultaneous or successive stretching in the same way as in monoaxial stretching. The uniform stretching and the formation of pores can be achieved with a stretch ratio of 1.1 in at least one direction. The stretch ratio with which the formation of pores and uniform stretching can be achieved is 1.1 to 3.0 in at least one direction.

After uniaxial stretching or biaxial stretching, the obtained film is subjected to heat-set at a temperature of 100° to 180° C., preferably 100° to 110° C., so that the dimensional accuracy of the film can be stabilized. Surface treatment known as corona treatment or flame treatment can also be performed.

In the present invention, the thickness of the porous film is 0.01 to 0.5 mm, preferably 0.02 to 0.3 mm. The porous film of the present invention has tear strength (MD) of not less than 10 Kg cm/cm$^2$ and permeability of not less than 1000 g/m$^2$.24 hrs.

Absorbent sanitary articles according to the present invention comprise a liquid impermeable back sheet of the porous film obtained by melt-forming the composition containing the polyolefin resin, the filler and the ester of dipentaerythritol, and then stretching the formed film, a liquid absorber, and a liquid permeable surface sheet, the liquid absorber being interposed between the liquid impermeable back sheet and the liquid permeable surface sheet.

A gauze or a non-woven fabric is used in the liquid permeable surface sheet which directly contacts with a skin. It is preferable to use a non-woven fabric made of polyolefin fibers such as polypropylene fibers or polyester fibers.

The liquid absorber is interposed between the liquid impermeable back sheet and the liquid permeable surface sheet, and absorbing paper, pulp paper or a highly absorbent polymer is used as the liquid absorber. It is preferable to place one liquid absorber sheet on the other for improving permeability to air so that the bulk density is increased. The thickness of the absorber is generally 5 to 20 mm.

In addition, a pressure sensitive tape is used for fitting and an expansion member such as rubber is used in the portions around the crotch for preventing any leakage therefrom.

The method for producing the porous film according to the present invention has the following advantages:

(1) The formation of many pores can be achieved with a low stretch ratio.

(2) Stretching stress is low and low-temperature stretching is possible.

(3) Uniform stretching can be performed with a low stretch ratio.

The porous film according to the present invention has the following advantages:

(1) Substantially no stretching spots are found.

(2) The permeability to water vapor and permeability to gases are excellent, and the water-resistance pressure is high.

(3) The flexibility is excellent.

(4) The anisotropy of the physical properties is small.

(5) The tear strength and the tensile strength are high.

(6) The adhesive strength of the ink printed on the film and the abrasion resistance thereof are high, i.e., the printing properties are excellent.

(7) The heat sealing properties are excellent and shrink package is possible.

(8) No bleeding of the third component on the film surfaces takes place with passage of time, and thus no trouble occurs in printing and other secondary processing.

(9) The film is easily incinerated and generates no harmful gas.

The porous film can be used in a permeable leakproof cover sheet for a paper diaper, as well as various applications such as clothing, packages, battery separators, filtering media and medical materials.

The absorbent sanitary articles such as a disposable diaper and the like according to the present invention have the liquid impermeable back sheet exhibiting the following advantages:

i) Substantially no stretching spots are found and there is uniformity in stretching, so that thus the sheet is visually attractive.

ii) The permeability to water vapor and the practical strength are excellent.

iii) The flexibility and feeling are excellent.

iv) No bleeding of the third component occurs and no trouble occurs during use.

v) The sheet is easily incinerated and generates no harmful gas.

Therefore, the disposable diaper according to the present invention exhibits excellent appearance and practical performance, and has a great value as a commercial product.

The present invention is described in detail below with reference to examples, but the present invention is not limited to the examples below.

The raw materials used in the examples and the comparative examples described below are shown in Tables 1 to 4.

TABLE 1

| Symbol | Polyolefin resin | Melt index (g/10 min.) | Density (g/cm³) |
|---|---|---|---|
| A-1 | Linear low-density polyethylene | 1.0 | 0.920 |
| A-2 | Linear low-density polyethylene | 2.0 | 0.921 |
| A-3 | High-density polyethylene | 0.2 | 0.946 |

(Note)
MI (melt index); measured at 190° C. in accordance with ASTM D 1238-70.
Density; measured at 20° C. by a density gradient tube in accordance with ASTM D 1505.

TABLE 2

| Symbol | Filler |
|---|---|
| B-1 | Calcium carbonate subjected to surface treatment with a saturated fatty acid |
| B-2 | Barium sulfate |
| B-3 | Talc |

TABLE 3

| Symbol | Third component (ratio of residual OH groups) | |
|---|---|---|
| C-1 | Dipentaerythritol enanthate | (5%) |
| C-2 | " | (20%) |
| C-3 | " | (30%) |
| C-4 | " | (40%) |
| C-5 | " | (60%) |
| C-6 | Dipentaerythritol 2-ethylhexanoate | (40%) |
| C-7 | Dipentaerythritol n-octanoate | (40%) |
| C-8 | Dipentaerythritol laurate | (40%) |
| C-9 | Dipentaerythritol stearate | (40%) |
| D-1 | Dipentaerythritol enanthate | (0%) |
| D-2 | " | (75%) |
| D-3 | " | (90%) |
| D-4 | Dipentaerythritol 2-ethylhexanoate | (0%) |
| D-5 | " | (2%) |
| D-6 | " | (80%) |
| D-7 | Dipentaerythritol n-octanoate | (0%) |
| D-8 | Dipentaerythritol stearate | (0%) |
| D-9 | " | (90%) |

$$\text{Ratio of residual OH group} = \frac{\text{Number of residual OH groups}}{\text{Total number of OH groups of alcohol}} \times 100(\%)$$

Number of the residual OH groups: measured in accordance with JIS K 0070

TABLE 4

| Number | Third component (ratio of residual OH groups: 0%) |
|---|---|
| C-10 | Dipentaerythritol hexaoctanoate |
| C-11 | Dipentaerythritol hexastearate |
| C-12 | Dipentaerythritol trioctanoate/tribenzoate |
| C-13 | Dipentaerythritol hexabenzoate |
| C-14 | Pentaerythritol tetraoctanoate |
| C-15 | Dioctylphthlate (DOP) |
| C-16 | Dioctyladipate (ODA) |
| C-17 | Epoxidized soybean oil |
| C-18 | Polyether polyol |
| C-19 | Isocyanate polyester polyol |
| C-20 | Paraffinic process oil |

EXAMPLES 1 TO 13 AND COMPARATIVE EXAMPLES 1 TO 14

Each of the polyolefin resins shown in Table 1 and each of the fillers shown in Table 2 were mixed under agitation in a Henschel mixer, and each of the third components shown in Table 4 was added to the obtained mixture and mixed therewith under agitation to obtain a mixture. The compositions of the thus-obtained mixtures are shown in Tables 5 and 6.

Each of the obtained mixtures was kneaded by a biaxial kneader (PCM-30, produced by Ikegai Steel Co., Ltd.), pelletized and then subjected to blown film molding using an extruder of 40 mm φ under the conditions described below to obtain a raw film having a thickness of 70 μm.

Cylinder tempertaure: 170°-190°-190° C.
Head and die temperature: 200° C.
Die bore diameter: 100 mm
Take-off speed: 8 m/min
Blow ratio: 2.0

The thus-obtained film was uniaxially stretched (machine direction) by means of a roll stretching machine.

The moldabilities during pelletization and formation of the raw film, the stretching temperature, the minimum stretching ratio ($\lambda_{MIN}$) with which uniform stretching and formation of many pores were performed, and the physical properties of the film at $\lambda_{MIN}$ are shown in Tables 7 and 8.

As can be seen from Tables 7 and 8, there are differences in the moldabilities and the stretching properties between the cases using the esters of dipentaerythritol as a third component and the cases using plasticizers. When the plasticizers are used, although molding is possible, the $\lambda_{MIN}$ values are increased and the degrees of longitudinal orientation (machine direction) of the stretched films are consequently increased, resulting in decreases in the longitudinal tear strength and transverse tear strength. Therefore, the physical properties such as the permeability and the strength is out of balance, leading to a disadvantage according to application.

TABLE 5

| Example | Polyolefin resin Type | Kg | Filler Type | Kg | Third Component Type | Kg |
|---|---|---|---|---|---|---|
| 1-3 | A-1 | 3.5 | B-1 | 6.0 | C-10 | 0.7 |
| 4 | " | " | " | " | C-11 | " |
| 5, 6 | " | " | " | " | C-12 | " |
| 7 | " | " | " | " | C-13 | " |
| 8, 9 | " | 3.9 | " | 5.6 | C-10 | " |
| 10 | A-2 | 4.5 | " | 5.0 | " | " |
| 11, 12 | A-3 | 3.5 | " | 6.0 | " | 1.0 |
| 13 | A-1 | 3.7 | B-2 | 5.8 | " | 0.7 |

TABLE 6

| Comparative Example | Polyolefin resin Type | Kg | Filler Type | Kg | Third Component Type | Kg |
|---|---|---|---|---|---|---|
| 1 | A-1 | 3.5 | B-1 | 6.0 | C-14 | 0.7 |
| 2 | " | " | " | " | C-15 | " |
| 3 | " | " | " | " | C-16 | " |
| 4 | " | " | " | " | C-17 | " |
| 5 | " | " | " | " | " | 0.2 |
| 6, 8 | " | " | " | " | C-15 | 1.0 |
| 7 | " | " | " | " | " | 1.5 |
| 9 | " | " | " | " | C-18 | 0.7 |
| 10 | " | " | " | " | C-19 | " |
| 11 | " | " | " | " | C-20 | " |
| 12 | " | 1.5 | " | 7.5 | C-10 | " |
| 13 | " | 2.5 | " | 4.5 | " | 3.0 |
| 14 | " | 3.5 | " | 6.0 | — | — |

TABLE 7

| Example | Pelletization Biaxial kneading property | Formation of raw film Uniform fluidity | Formation of raw film Bubble stability | Stretching temperature (°C.) | $\lambda_{MIN}$ | Thickness (μm) | Tensile strength (MD/TD) (Kg/cm²) | Tear strength (MD) (Kg cm/cm²) | Permeability (g/m² · 24 hrs) | Flexibility |
|---|---|---|---|---|---|---|---|---|---|---|
| 1  | ◯ | ◯ | ◉ | 70 | 2.0 | 58 | 125/62 | 17.5 | 3840 | ◉ |
| 2  | ◯ | ◯ | ◉ | 50 | 1.7 | 63 | 117/70 | 22.5 | 3810 | ◯ |
| 3  | ◯ | ◯ | ◉ | 90 | 2.5 | 51 | 141/51 | 8.3  | 3670 | ◉ |
| 4  | ◯ | ◯ | ◉ | 70 | 2.1 | 57 | 125/60 | 17.0 | 3870 | ◉ |
| 5  | ◯ | ◯ | ◉ | "  | 2.0 | 58 | 122/59 | 16.0 | 3740 | ◉ |
| 6  | ◯ | ◯ | ◉ | 50 | 1.8 | 62 | 119/65 | 18.0 | 3700 | ◯ |
| 7  | ◯ | ◯ | ◯ | 70 | 2.1 | 57 | 125/57 | 13.5 | 3730 | ◯ |
| 8  | ◯ | ◯ | ◉ | "  | 2.4 | 52 | 140/61 | 11.5 | 3970 | ◉ |
| 9  | ◯ | ◯ | ◉ | 50 | 2.0 | 58 | 130/65 | 17.8 | 3830 | ◉ |
| 10 | ◯ | ◯ | ◉ | "  | 2.5 | 50 | 134/51 | 7.8  | 4350 | ◉ |
| 11 | ◯ | ◯ | ◯ | 80 | 2.1 | 57 | 129/63 | 12.1 | 3720 | ◯ |
| 12 | ◯ | ◯ | ◉ | 60 | 2.0 | 59 | 127/63 | 12.5 | 3970 | ◯ |
| 13 | ◯ | ◯ | ◉ | 70 | 2.2 | 56 | 128/61 | 15.0 | 3660 | ◉ |

TABLE 8

| Comparative example | Pelletization Biaxial kneading property | Formation of raw film Uniform fluidity | Formation of raw film Bubble stability | Stretching temperature (°C.) | $\lambda_{MIN}$ | Thickness (μm) | Tensile strength (MD/TD) (Kg/cm²) | Tear strength (MD) (Kg cm/cm²) | Permeability (g/m² · 24 hrs) | Flexibility |
|---|---|---|---|---|---|---|---|---|---|---|
| 1  | ◯ | ◯ | ◉ | 70 | 3.5 | 34 | 150/34 | 4.7 | 5060 | ◉ |
| 2  | ◯ | ◯ | ◯ | "  | 4.0 | 30 | 155/28 | 4.1 | 5320 | ◉ |
| 3  | ◯ | ◯ | ◯ | "  | 4.5 | 28 | 157/27 | 4.0 | 5360 | ◉ |
| 4  | ◯ | X |   |    |     |    |        |     |      |   |
| 5  | ◯ | ◯ | ◯ | 70 | 3.3 | 37 | 151/33 | 4.5 | 5210 | ◉ |
| 6  | ◯ | ◯ | △ | "  | 3.5 | 33 | 151/32 | 4.4 | 5130 | ◉ |
| 7  | ◯ | ◯ | X |    |     |    |        |     |      |   |
| 8  | ◯ | ◯ | △ | 50 | 3.4 | 35 | 146/33 | 4.5 | 5170 | ◉ |
| 9  | ◯ | X |   |    |     |    |        |     |      |   |
| 10 | X |   |   |    |     |    |        |     |      |   |
| 11 | ◯ | ◯ | ◉ | 70 | 5.0 | 25 | 151/24 | 3.3 | 5370 | ◉ |
| 12 | △ | X | X |    |     |    |        |     |      |   |
| 13 | X |   |   |    |     |    |        |     |      |   |
| 14 | ◯ | ◯ | ◉ | 70 | 6.0 | 23 | 162/21 | 2.5 | 5410 | ◉ |

EXAMPLES 14 TO 24 AND COMPARATIVE EXAMPLES 15 TO 23

Each of the polyolefin resins shown in Table 1 and each of the fillers shown in Table 2 were mixed under agitation in a Henschel mixer, and each of the third components shown in Table 3 was added to the obtained mixture and mixed therewith under agitation to obtain a mixture. The compositions of the thus-obtained mixtures are shown in Tables 9 and 10.

Each of the obtained mixtures was kneaded by a biaxial kneader (PCM-45, produced by Ikegai Steel Co., Ltd.), pelletized and then subjected to blown film extruding using an extruder of 40 mm φ under the conditions described below to obtain a raw film having a thickness of 70 μm.

Cylinder tempertaure: 170°-190°-190° C.
Head and die temperature: 200° C.
Die bore diameter: 100 mm
Take-off speed: 8 m/min
Blow ratio: 2.0

The thus-obtained film was uniaxially stretched (machine direction) at 60° C. by means of a roll stretching machine.

The moldabilities during pelletization and formation of the raw film, the stretching temperature, the minimum stretching ratio ($\lambda_{MIN}$) with which uniform stretching and formation of many pores were performed, and the physical properties of the film at $\lambda_{MIN}$ are shown in Tables 11 and 12.

As can be seen from Tables 11 and 12, there are differences in the moldabilities and the stretching properties between the cases using the esters of dipentaerythritol as a third component and the cases using plasticizers. When the plasticizers are used, although molding is possible, the $\lambda_{MIN}$ values are increased and the degrees of longitudinal orientation (machine direction) of the stretched films are consequently increased, resulting in decreases in the longitudinal tear strength and transverse tear strength. Therefore, the physical properties such as the permeability and the strength is out of balance, leading to a disadvantage according to application.

TABLE 9

| Example | Polyolefin resin Type | Polyolefin resin Kg | Filler Type | Filler Kg | Third component Type | Third component Kg |
|---|---|---|---|---|---|---|
| 14 | A-1 | 3.5 | B-1 | 6.0 | C-1 | 0.4 |
| 15 | "   | "   | "   | "   | C-2 | "   |
| 16 | "   | "   | "   | "   | C-4 | "   |
| 17 | "   | "   | "   | "   | C-5 | "   |
| 18 | "   | "   | "   | "   | C-6 | "   |
| 19 | "   | "   | "   | "   | C-7 | "   |
| 20 | "   | "   | "   | "   | C 8 | "   |
| 21 | "   | "   | "   | "   | C-9 | "   |
| 22 | A-2 | 3.5 | "   | "   | C-2 | "   |
| 23 | A-3 | 3.5 | "   | "   | C-3 | 0.6 |

TABLE 9-continued

| Example | Polyolefin resin Type | Kg | Filler Type | Kg | Third component Type | Kg |
|---|---|---|---|---|---|---|
| 24 | A-1 | 3.5 | B-2 | 6.0 | C-3 | 0.4 |

TABLE 10

| Comparative Example | Polyolefin resin Type | Kg | Filler Type | Kg | Third component Type | Kg |
|---|---|---|---|---|---|---|
| 15 | A-1 | 3.5 | B-1 | 6.0 | D-1 | 0.4 |
| 16 | " | " | " | " | D-2 | " |
| 17 | " | " | " | " | D-3 | " |
| 18 | " | " | " | " | D-4 | " |
| 19 | " | " | " | " | D-5 | " |
| 20 | " | " | " | " | D-6 | " |
| 21 | " | " | " | " | D-7 | " |
| 22 | " | " | " | " | D-8 | " |
| 23 | A-1 | 3.5 | B-1 | 6.0 | D-9 | 0.4 |

TABLE 11

| Example | Raw film-forming property Uniform fluidity | Raw film-forming property Bubble stability | Strechability λMIN | Physical property of film Tear strength (MD) (Kg·cm/cm²) | Physical property of film Permeability (g/m²·24 hrs) | Flexibility | Ink adhesion |
|---|---|---|---|---|---|---|---|
| 14 | ○ | ⊙ | 2.00 | 17.0 | 4560 | ⊙ | ○ |
| 15 | ○ | ⊙ | 1.90 | 20.0 | 4440 | ⊙ | ⊙ |
| 16 | ○ | ⊙ | 1.83 | 22.0 | 4270 | ⊙ | ⊙ |
| 17 | ○ | ○ | 1.81 | 22.2 | 4200 | ⊙ | ⊙ |
| 18 | ○ | ⊙ | 1.88 | 20.6 | 4390 | ⊙ | ⊙ |
| 19 | ○ | ⊙ | 1.85 | 21.3 | 4320 | ⊙ | ⊙ |
| 20 | ○ | ⊙ | 1.90 | 20.2 | 4370 | ⊙ | ○ |
| 21 | ○ | ⊙ | 2.00 | 17.8 | 4390 | ⊙ | ⊙ |
| 22 | ○ | ⊙ | 1.96 | 16.1 | 5110 | ⊙ | ⊙ |
| 23 | ○ | ⊙ | 1.95 | 13.8 | 4270 | ○ | ⊙ |
| 24 | ○ | ⊙ | 1.87 | 19.2 | 4490 | ⊙ | ⊙ |

TABLE 12

| Comparative example | Raw film-forming property Uniform fluidity | Raw film-forming property Bubble stability | Strechability λMIN | Physical property of film Tear strength (MD) (Kg·cm/cm²) | Physical property of film Permeability (g/m²·24 hrs) | Flexibility | Ink adhesion |
|---|---|---|---|---|---|---|---|
| 15 | ○ | ⊙ | 2.50 | 8.0 | 5160 | ⊙ | X X |
| 16 | ○ | X | | | | | |
| 17 | X | X | | | | | |
| 18 | ○ | ⊙ | 2.65 | 6.8 | 5280 | ⊙ | X X |
| 19 | ○ | ⊙ | 2.60 | 7.1 | 5230 | ⊙ | X |
| 20 | X | X | | | | | |
| 21 | ○ | ⊙ | 2.60 | 7.2 | 5230 | ⊙ | X X |
| 22 | ○ | ⊙ | 2.85 | 5.1 | 5780 | ⊙ | X X |
| 23 | X | X | | | | | |

The methods of measureing the moldability and the physical properties shown in Tables 7, 8, 11 and 12 are as follows:

Moldability

1) Biaxial kneading property during pelletization
○: Stable pelletization is possible without producing venting up and surging
X: Stable pelletization is impossible because of the occurrence of venting up and surging
2) Uniform fluidity during formation of a raw film
○: A molten resin is uniformly discharged from the whole periphery of a die clearance during blown film extruding
X: Stable molding is impossible because a molten resin is not uniformly discharged from the whole periphery of a die clearance.
3) Bubble stability during formation of a raw film
⊙: Bubbles do not sway.
○: Bubbles substantially do not sway.
Δ: Bubbles sway, but formation of a film is possible.
X: Bubbles vigourously sway, and formation of a film is difficult.

(Physical properties)

1) Tensile strength
In accordance with ASTM D 882 (Condition E),
10 mm width×50 mm length,
Tensile speed: 500 mm/min
2) Tear strength
In accordance with JIS P-8116, the strength of a film in the machine direction thereof is measured.
Sample size: 63 mm width×76 mm lenght
Notch length: 20 mm
3) Permeability
In accordance with JIS Z 0208
At 30° C., 90% RH
4) Flexibility
This is measured by feeling with the hands and decided on the basis of the following criteria:
⊙: Very soft
○: Soft
Δ: Slightly hard X: Hard 5) Printing property (ink adhesion)

Evaluation is made in accordance with the following procedure:

(i) Preparation of ink

An ink used for an untreated polyolefin, Polymate G. T. (trade name), produced by Toyo Ink Manufacturing Co., Ltd. is diluted with a solvent GN502 used for dilution so that the ratio of the ink to the solvent is 1:1 (by weight).

(ii) Solid printing

An ink is dropped on a film, and solid printing is then performed by using a #8 bar coater (the diameter of the core of the bar coater: 8/1000 inch).

(iii) Drying

Drying with air is performed at room temperature for 24 hours.

(iv) Adhesion of cellophane tape

A cellophane tape is adhered to a film on which an ink is applied while being pressed by a rubber roller.

(v) Judgment of ink adhesion

The adhered cellophane tape is immediately separated from the film, and judgement is made on the basis of the area ratio of the ink remaining on the film.

| Mark | Ratio of residual area |
|------|------------------------|
| ⊚ | 95% or more |
| ○ | 60% or more and less than 95% |
| Δ | 20% or more and less than 60% |
| X | 5% or more and less than 20% |
| X X | less than 5% | of the fillers shown in Table 2 were mixed under agitation in a Henschel mixer, and each of the third component shown in Table 4 was added to the obtained mixture and mixed under agitation to obtain a mixture.

The thus-obtained mixture was kneaded by means of a biaxial kneader (PCM-30, produced by Ikegai Steel Co., Ltd.), pelletized and then subjected to blown film extruding by an extruder of 50 mm φ under the conditions described below to obtain a raw film having a thickness of 70 μm.

Cylinder temperature: 170°–190°–190° C.
Head and die temperature: 200° C.
Die bore diameter: 150 mm
Take-off speed: 10 m/min
Blow ratio: 2.5

The thus-obtained film was uniaxially stretched (machine direction) by using a roll stretching machine to obtain a sheet having many pores.

A liquid absorber comprising a sheet of pulp paper and an a water absorbing polymer, and a liquid permeable surface sheet composed of a non-woven polyester fabric were placed on the thus-formed liquid impermeable back sheet in order, and these superposed sheets were united. A pressure sensitive tape and a stretch rubber member are provided on the united sheets to form a disposable diaper.

The moldability, stretch ratio, appearance and physical properties of each of the liquid impermeable back sheets formed, and the results of wearing of the disposable diapers of the present invention are shown in Tables 13 and 14.

The method of measuring each of the evaluation items and the criteria for judging are described below.

TABLE 13

| Example | Polyolefin resin Type | Polyolefin resin Amount* | Filler Type | Filler Amount* | Plasticizer Type | Plasticizer Amount* | Moldability | Stretch ratio |
|---------|------|---------|------|---------|------|---------|--------|--------|
| 25 | A-1 | 100 | B-1 | 170 | C-10 | 20 | ○ | 2.0 |
| 26 | " | " | " | " | C-11 | " | ○ | 2.1 |
| 27 | " | " | " | " | C-12 | " | ○ | 2.0 |
| 28 | " | " | " | " | C-13 | " | ○ | 2.1 |
| 29 | " | " | " | 140 | C-10 | " | ○ | 2.3 |
| 30 | A-2 | " | " | 110 | " | " | ○ | 2.5 |
| 31 | A-3 | " | " | 170 | " | 30 | ○ | 2.1 |
| 32 | A-1 | " | B-2 | 150 | " | 18 | ○ | 2.0 |
| 33 | A-1 | 100 | B-1 | 110 | C-10 | 15 | ○ | 2.0 × 2.5 |

| Example | Appearance of sheet unevenness in streching | Appearance of sheet Flexibility | Physical properties of sheet Permeability (g/m² · 24 hr) | Physical properties of sheet Tear strength (Kg cm/cm²) | Result of use of diaper Eruption | Result of use of diaper Breakage |
|---------|------|------|------|------|------|------|
| 25 | ○ | ○ | 3850 | 17.0 | No | No |
| 26 | ○ | ○ | 3860 | 16.9 | " | " |
| 27 | ○ | ○ | 3750 | 16.1 | " | " |
| 28 | ○ | ○ | 3750 | 13.7 | " | " |
| 29 | ○ | ○ | 4010 | 11.8 | " | " |
| 30 | ○ | ○ | 4310 | 10.2 | " | " |
| 31 | ○ | ○~Δ | 3780 | 11.8 | " | " |
| 32 | ○ | ○ | 3450 | 15.5 | " | " |
| 33 | ⊚ | ⊚ | 5130 | 35.0 | No | No |

*Parts by weight

EXAMPLES 25 TO 32 AND COMPARATIVE EXAMPLES 24 TO 30

When a liquid impermeable back sheet was formed, each of the polyolefin resins shown in Table 1 and each

TABLE 14

| Compara- | Composition of raw material |

TABLE 14-continued

| Comparative example | Polyolefin resin Type | Polyolefin resin Amount* | Filler Type | Filler Amount* | Plasticizer Type | Plasticizer Amount* | Moldability | Stretch ratio |
|---|---|---|---|---|---|---|---|---|
| 24[1] | A-1 | 100 | B-1 | 170 | C-15 | 20 | ○ | 2.5 |
| 25 | " | " | " | " | " | " | ○ | 4.0 |
| 26 | " | " | " | " | " | " | X | |
| 27[2] | " | " | " | " | C-17 | 10 | ○ | 2.5 |
| 28 | " | " | " | " | C-18 | 20 | X | |
| 29[3] | " | " | " | " | No | | ○ | 2.0 |
| 30 | " | " | " | " | No | | ○ | 6.0 |
| 31[4] | A-1 | 100 | B-1 | 120 | No | | ○ | 2.0 × 3.0 |

| Comparative example | Appearance of sheet — unevenness in streching | Appearance of sheet — Flexibility | Physical properties of sheet — Permeability (g/m² · 24 hr) | Physical properties of sheet — Tear strength (Kg cm/cm²) | Result of use of diaper — Eruption | Result of use of diaper — Breakage |
|---|---|---|---|---|---|---|
| 24[1] | X | Δ | 3510 | 15.5 | ○ | ○ |
| 25 | ○ | ○ | 5310 | 4.3 | ○ | X |
| 27[2] | Δ | ○ | 4560 | 9.3 | ○ | Δ |
| 29[3] | X | X | 4210 | 12.1 | Δ | ○ |
| 30 | ○ | Δ | 5130 | 2.1 | ○ | X |
| 31[4] | X | Δ | 5570 | 25.2 | ○ | ○ |

*Parts by weight
[1] With no value as a commercial product because of unevenness in stretching.
[2] With bleeding and poor feeling
[3] With no value as a commercial product because of unevenness in stretching.
[4] With no value as a commercial product because of unevenness in stretching.

(Moldability)

The moldability in compound molding (pelletization) and in film molding is collectively judged on the basis of the following criteria:

○: Stable molding is possible without producing any trouble in both compound molding and film molding.

X: Stable pelletization is impossible because venting up or surging occur during compound molding, or stable pelletization is possible but stable film molding is impossible because of non-uniform extrusion of a molten resin from a die opening or poor stability of bubbles during the film molding.

(Sheet appearance)

1) Uniformity in stretching (visual judgement)

◎: The whole film is completely and uniformly stretched and uniformly made porous, and uniformity is obserbed.

○: The film is substantially uniformly stretched and made porous, and thus substantially no unevenness is observed.

Δ: Non-uniformity is recognized to some extent but is not remarkable.

X: Non-uniform stretching and non-uniform whitening are observed over the whole film, and the appearance is not so good.

2) Flexibility (judged by the touch with the hands)
◎: Extremely flexible and extremey good feeling
○: Flexible
Δ: Slightly hard
X: Hard and poor feeling (Physical properies)

1) Permeability
In accordance with JIS Z 0208 (at 30° C., 90% RH)
2) Tear strength
In accordance with JIS P-8116, the strength of a film in the machine direction is measured.
Sample size: 63 mm width×76 mm length
Notch length: 20 mm

EXAMPLE 33 AND COMPARATIVE EXAMPLE 31

When a liquid impermeable back sheet was formed, after a compound had been pelletized by the aforementioned method, the formed pellets were then subjected to T-die molding by an extruder of 65 mm φ under the conditions described below to form a raw film having a thickness of 90 μm.

Cylinder temperature: 170°–190°–190° C.
Head and die temperature: 230° C.
T-die lip width: 450 mm
Take-off speed: 16 m/min The thus-obtained film was stretched (machine direction) by a roll stretching machine, and then stretched (transversal direction) by a tenter to obtain a porous sheet.

A disposable paper diaper was formed by using the formed liquid impermeable back sheet in the same way as that described above.

The moldability, appearance and physical properties of each of the liquid impermeable back sheets and the results of use of the disposable diapers formed by using the sheets are shown in Tables 13 and 14.

As can be seen from comparison between Tables 13 and 14, there are differences in the moldability, appearance and physical properties of the sheets between the case using the ester of dipentaerythritol as a third component and the case using the plasticizer which is added to the composition for each of the liquid impermeable back sheets.

Accordingly, there are differences in performance between the diapers formed by using these back sheets. Therefore, the disposable diapers in accordance with the present invention are excellent as commercial products because of their good quality and appearance.

What is claimed is:

1. A process for producing a porous film having a tear strength (MD) of not less than 10 kg.cm/cm², a permeability of not less than 1000 g/m².24 hrs and a thickness from 0.01 to 0.5 mm, which comprises the steps of:
  melt-molding a composition containing 100 parts by weight of a polyolefin resin, 25 to 400 parts by weight of a filler having an average particle size of 30 μm or less and 1 to 30 parts by weight of an ester of dipentaerythritol having a ratio of residual OH groups of 3 to 70% to obtain a sheet, and
  stretching the sheet at 40° to 170° C. in at least one direction by 1.1 to 3.0 times.

2. A process according to claim 1, wherein said stretching is uniaxial stretching, biaxial stretching or multi-stage stretching.

3. A process according to claim 1, further comprising subjecting the stretched film to heat-treatment at 100° to 180° C.

4. A process according to claim 1, further comprising subjecting the stretched film to corona-treatment or flame-treatment.

5. A process according to claim 1, wherein said polyolefin resin is polyethylene or crystalline polypropylene.

6. A process according to claim 5, wherein said polyethylene has a melt index of 0.01 to 10 g/10 minutes.

7. A process according to claim 5, wherein said polyethylene is high-density polyethylene, medium-density polyethylene, low-density polyethylene or a mixture thereof.

8. A process according to claim 5, wherein said crystalline polypropylene is a propylene homopolymer, a copolymer of propylene and any other α-olefin, or a mixture thereof.

9. A process according to claim 1, wherein said filler is an inorganic filler or an organic filler.

10. A process according to claim 6, wherein said inorganic filler is calcium carbonate, talc, clay, kaolin, silica, diatomaceous earth, magnesium carbonate, calcium sulfate, aluminium hydroxide, zinc oxide, magnesium hydroxide, calcium oxide, magnesium oxide, titanium oxide, alumina, mica, asbestos powder, glass powder, shirasu ballon, zeolite or silica clay.

11. A process according to claim 6, wherein said organic filler is cellulose powder such as wood powder or pulp.

12. A process according to claim 1, wherein said filler is subjected to surface treatment with a fatty acid or a metal salt thereof.

13. A process according to claim 9, wherein the amount of said fatty acid or said metal salt thereof used for surface treatment of said filler is not more than 10 parts by weight based on 100 parts by weight of said filler.

14. A process according to claim 1, wherein said ester of dipentaerythritol is an ester of dipentaerythritol with an aliphatic mono- or dicarboxylic acid having 1 to 30 carbon atoms or with an aromatic mono- or dicarboxylic acid having 7 to 16 carbon atoms.

15. A process according to claim 11, wherein said aliphatic carboxylic acid is acetic acid, propionic acid, butyric acid, isobutyric acid, valeric acid, isovaleric acid, capronic acid, isocapronic acid, 2-ethylbutanoic acid, enanthic acid, caprilic acid, lauric acid, tridecanoic acid, myristic acid, pentadecanoic acid, palmitic acid, stearic acid, eicosanoic acid, behenic acid, cerotic acid, melissic acid, succinic acid, glutaric acid, adipic acid, azelaic acid or sebacic acid.

16. A process according to claim 14, wherein said aromatic carboxylic acid is benzoic acid, phthalic acid, isophthalic acid or terephthalic acid.

17. A process according to claim 1, wherein said composition contains 100 parts by weight of said polyolefin resin, 100 to 300 parts by weight of said filler and 3 to 20 parts by weight of said ester of dipentaerythritol.

* * * * *